United States Patent [19]

George et al.

[11] 3,981,200

[45] Sept. 21, 1976

[54] METHOD OF AUTOMATICALLY TRANSFERRING AND INJECTING A LIQUID SAMPLE

[75] Inventors: Richard Alexander George; Adriaan Herman Hubert van Abel, both of Eindhoven, Netherlands

[73] Assignee: U.S. Philips Corporation, New York, N.Y.

[22] Filed: Aug. 29, 1975

[21] Appl. No.: 609,012

[30] Foreign Application Priority Data

Sept. 2, 1974  Netherlands ...................... 7411605

[52] U.S. Cl. ............................................ 73/422 GC
[51] Int. Cl.² ........................................... G01N 1/10
[58] Field of Search ............... 73/422 GC, 425.4 P, 73/425.6, 61.1 C; 210/198 C; 141/329

[56] References Cited

UNITED STATES PATENTS

| 3,474,674 | 10/1969 | Harris .......................... 73/422 GC |
| 3,733,909 | 5/1973 | Golovistikov .................. 73/422 GC |
| 3,834,240 | 9/1974 | Kenney ............................ 73/425.6 |
| 3,842,680 | 10/1974 | Vollick et al. ................. 73/425.4 P |

*Primary Examiner*—S. Clement Swisher
*Attorney, Agent, or Firm*—Frank R. Trifari; David R. Treacy

[57] ABSTRACT

A method of transferring and injecting a liquid sample, by supplying an inert gas to an injection needle after normal injection has taken place by the action of a plunger. The injection syringe is constructed to allow the inert gas to pass freely even when the needle is fully depressed, to remove any drop clinging to the tip or needle inner wall.

4 Claims, 4 Drawing Figures

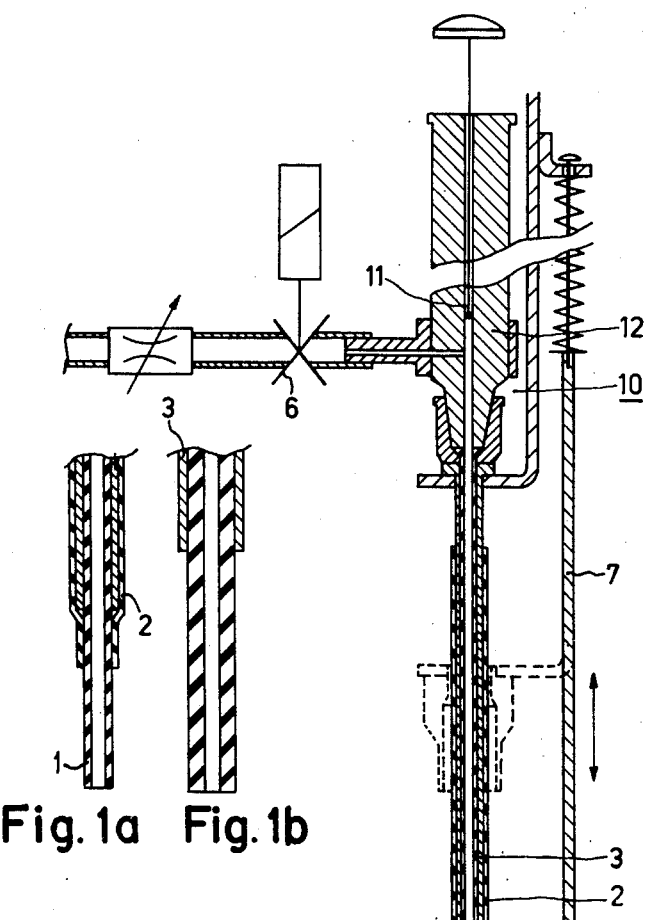
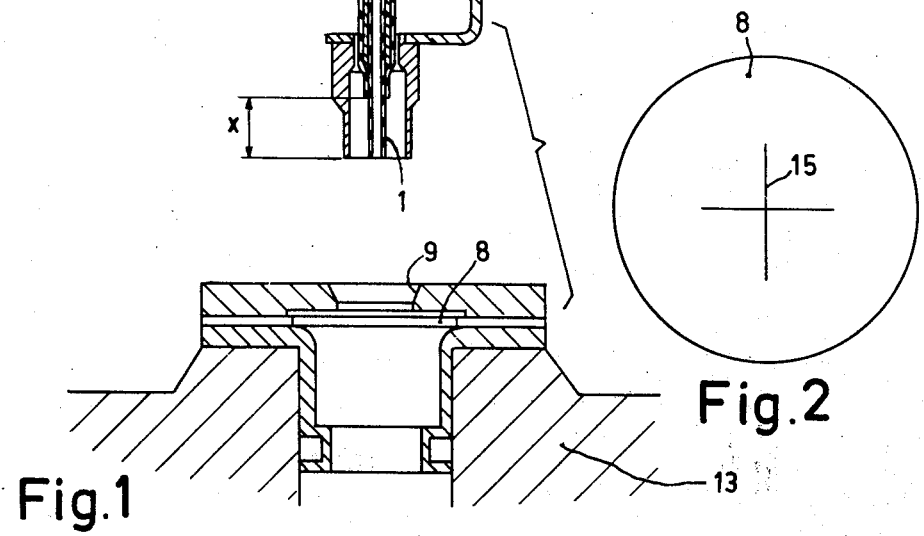
Fig. 1a  Fig. 1b
Fig. 1
Fig. 2

METHOD OF AUTOMATICALLY TRANSFERRING AND INJECTING A LIQUID SAMPLE

BACKGROUND OF THE INVENTION

1. Field of the Invention

The invention relates to a method of automatically transferring and injecting a liquid sample with the aid of an injection syringe. The invention also relates to a device for carrying out this method and to an atomic absorption spectrometer which includes said device.

2. Description of the Prior Art

It is known to fill injection syringe manually and expel its contents into a receiver; for example, in the case of a device for atomic absorption spectroscopy, to inject the contents (generally between 1 and 100 μl of sample liquid) into the furnace, for which openings or valves in the furnace housing have to be opened and closed. This method has the drawback that minor differences in the position in which the injection syringe is disposed in the furnace give rise to variations in the measuring results.

In atomic absorption spectrometry it is common practice to automate a number of operations, such as programming of the temperature variation of the furnace. It is also known to fill the furnace automatically and periodically with a sample of the substance to be examined. According to the method known from the journal "Analyst", Volume 97, pages 647-652, the liquid sample is transferred from a first pipe by means of a suitable sliding valve to a second pipe is connected to the furnace by a quartz capillary.

The sample is automatically blown into the furnace with the inert carrier gas argon, which flows through the second pipe. The known method is suitable for the analysis of samples which can be made to flow continuously into the second pipe via the sliding valve. However, the method is not suitable for the examination of sample in vials which contain very small amounts of sample liquid. A further drawback of that known method is that the comparatively low amount of sample liquid must be blown through a comparatively long tube before it can reach the furnace. During transport through said tube liquids may coagulate or foam, as a result of which the samples supplied to the furnace are not readily reproducible. Indeed, cross-contamination may arise owing to extremely small droplets of the sample liquid which are left behind in the tube.

Furthermore, experiments have taught that an injection needle, of which at least the inner wall is made of a metallic material, may affect the metal concentration of the sample liquid if the metal concentration in said liquid is a few parts per million or less. The extent to which said concentration is affected inter alia depends on the element to be analysed, the acidity of the sample and the choice of the metal of the needle. Generally, the effect is appreciable, and, moreover, the magnitude of the effect is not reproducible.

Furthermore, it is not desirable to bring the sample liquids into contact with metal at locations other than the inner wall of the injection needle, for example the metal of the cylinder or the plunger of the injection syringe. When the injection syringe is filled, i.e. when the plunger of the injection syringe is withdrawn to cause the liquid to be drawn into the injection needle, care must be taken that the liquid remains in the injection needle. Moreover, the liquid sample must be injected completely. In other words: no drop of liquid should be left on the injection needle.

SUMMARY OF THE INVENTION

It is an object of the invention to mitigate the above-mentioned drawbacks, and to meet the above-mentioned requirements, respectively. For this, a method according to the invention is characterized in that complete injection of the liquid sample into a receiver is achieved by supplying an inert gas to the injection needle after normal injection has taken place by the action of a plunger, which plunger in any position allows the inert gas to pass freely through the injection needle.

A device for carrying out the methods is characterized in that the internal volume of the injection needle is greater than the volume of the liquid sample and that a gas source, which supplies the inert gas, is connected to the injection needle via a valve.

BRIEF DESCRIPTION OF THE DRAWING

The invention will be described by way of example with reference to the drawing, in which:

FIG. 1 shows a device according to the invention,

FIGS. 1a and 1b being enlarged views of alternative needle constructions usable in the device, and FIG. 2 illustrates the stopper of the measuring apparatus of FIG. 1 in more detail.

DESCRIPTION OF THE PREFERRED EMBODIMENTS

The injection syringe 10 shown in FIG. 1 comprises a cylinder 12, a plunger 11 and an injection needle 1. Between the plunger 11 and the cylinder 12 gas-tight sealing exists. The needle 1 may be a comparatively thick-walled hollow tube of teflon or another non-metallic material, as shown in FIG. 1b. The teflon needle 1 may also have a comparatively thin wall. In that case, as shown in FIG. 1a, it is reinforced with a metal tube 3, which tightly surrounds the needle, which tube in its turn is surrounded by a teflon sleeve 2. (This is because the length of the needle should not be limited by the low rigidity of the material of the needle). In either case, the internal volume of the needle is greater than the volume of the liquid sample, which is for example 20 μl. When the syringe 10 is filled with the liquid to be examined, there will consequently be no contact of the liquid with the plunger 11 and with the connection of the needle 1 with the cylinder 12.

Care must be taken to avoid that when the needle 1 is emptied, i.e. during the depression of the plunger 11, a drop of the liquid remains on the needle. According to a feature of the invention the injection syringe 10 is therefore coupled to a gas source (not shown) via a solenoid-operated valve 6. The dead space between the valve 6 and the syringe 10 is kept as small as possible. When the syringe 10 is filled and the syringe is transferred to the furnace 13 the valve 6 is closed. The syringe 10 is brought into the furnace 13 and the plunger 11 is pressed down. The greater part of the liquid is forced out of the needle 1. The remainder is driven out of the needle by opening the valve 6 so that the gas from the gas source blows the residual liquid out of the needle 1. Subsequently, the syringe 10 is removed from the furnace 13. These operations are automatically controlled, for example with the aid of a computer program.

The liquid to be analysed which has been forced out of the needle 1 is collected in a crucible which is disposed in the center of the furnace 13. The crucible, which may reach a high temperature, must be protected against oxidization. For this purpose it is common practice to allow an inert gas to flow through the furnace. It is also common practice to supply new liquid to the crucible by removing a stopper in the furnace wall. According to another feature of the invention a stopper 8 having a seal which consists of an elastomer is used, which stopper is cut in the center, for example in the form of a cross 15 (FIG. 2).

Normally the stopper 8 is closed. When the injection syringe 10 is moved down, i.e. in the direction of the furnace 13, the syringe guide 7 comes into contact with the metal supporting ring 9 of the seal 8 of an elastomer compound, so that the needle 1 is centered relative to the stopper 8. When the syringe guide 7 is moved down further the flaps of the seal 8 are pushed open. The stopper 8 allows the needle 1 to pass through, the needle is automatically stopped a few millimeters above the crucible in the furnace 13, and is subsequently emptied. As the stopper 8 automatically centers the needle 1 relative to the crucible, there will be no deviations in the measuring results which would be caused by a variable position of the needle 1 relative to the crucible.

A further advantage of the device according to the invention is obtained during preparation. In particular if the liquid sample is of inhomogeneous composition, for example polluted river water, it will be necessary to stir said sample previously. This is effected in a simple manner. The injection syringe is inserted into the reservoir which contains the liquid to be analyzed. The gas from the gas source is supplied to the liquid via the valve 6 and the needle 1 which is immersed in the liquid. The liquid is then stirred by the gas. A sample of the correct composition may then be drawn into the needle 1.

What is claimed is:

1. A method for transferring and injecting a liquid sample into a receiver with the aid of an injection syringe having a plunger and a needle, comprising the sequential steps of drawing a liquid sample into the syringe by withdrawing the plunger, moving the syringe relative to the receiver so that the needle is disposed in the receiver, injecting the liquid sample by depressing the plunger, and passing an inert gas through the needle.

2. An injection syringe for transferring and injecting a liquid sample into a receiver, comprising a needle having a passage for receiving a liquid sample; a cylinder having a first passage portion, a second passage portion communicating with said first passage and with said needle passage, and a third passage communicating with said second passage; a plunger arranged in said first passage portion for reciprocable movement so as to draw liquid into said needle by movement to a withdrawn position and to expel liquid by movement to a depressed position; and means for allowing a gas to flow through said third passage into said second passage.

3. A syringe as claimed in claim 2 wherein an internal volume of said second and third passages is greater than a volume of sample to be injected, and said means for allowing includes a gas valve.

4. A syringe as claimed in claim 2 wherein said needle comprises a thin-walled tube of non-metallic material tightly surrounded by a metal tube.

* * * * *